United States Patent [19]
Cuero et al.

[11] Patent Number: 5,830,459
[45] Date of Patent: Nov. 3, 1998

[54] EFFECTIVE PLANT BIOCONTROL

[75] Inventors: Raul G. Cuero, Houston; Godson O. Osuji, Hockley, both of Tex.

[73] Assignee: Texas A&M University System, College Station, Tex.

[21] Appl. No.: 424,557

[22] Filed: Apr. 17, 1995

Related U.S. Application Data

[63] Continuation of Ser. No. 147,911, Nov. 4, 1993, which is a continuation of Ser. No. 954,448, Sep. 30, 1992, abandoned.

[51] Int. Cl.$^6$ .............................. A01N 63/00; A01G 7/00
[52] U.S. Cl. .................... 424/93.4; 424/93.47; 424/94.1; 47/58
[58] Field of Search ............................... 424/93 D, 93 R, 424/93 K, 93 N, 93 M, 93 Q, 94.1, 93.1, 93.4, 93.47; 47/57.6, 57.604, 57.605, 58

[56] References Cited

U.S. PATENT DOCUMENTS 4,798,723  1/1989  Dart et al. .................................. 424/93

OTHER PUBLICATIONS

Muzzarelli, R.A.A., "Carboxymethylated chitins and chitosans," *Carbohydrate Polymers* 8:1–21 (1988).
Hirano, S., et al., "Chitosan as an Ingredient for Domestic Animal Feeds," *J. Agric. Food Chem.* 38:1214–1217 (1990).
Cuero, R.G., Osuji, G., and Duffus, E., "N–Carboxymethylchitosan: Uptake and effect on chlorophyll production, water potential and biomass in tomato plants," *Food Biotech.* 5(2):95–103 (1991).
Allan. C.R. and Hadwiger, L.A., "The fungicidal effect of chitosan of fungi on varying cell wall composition," *Exp. Mycol.* 3:285–287 (1979).
Hadwiger, L.A., Fristensky, B., and Riggleman, R.C., "Chitosan, a natural regulator of plant–fungal pathogen interactions, increases crop yields," In *Chitin, chitosan, and related enzymes* (J.P. Zikakis, Ed.), pp. 291–302, Academic Press, Inc., New York, (1984).
Yabuki, M. Characterization of chitosanase produced by *Bacillus circulans* MH–K1. In *Chitin and Chitosanase Sources, Chemistry, Physical Properties and Applications* (G. Skjak–Braek, T. Anthonsen Conf. on Chitin and Chitosan, Trondheim, Norway, Aug. 22–24, 1988. Elsevier Applied Sciences, N.Y.) (1988).
Cuero, et al., "Aflatoxin control in preharvest maize; effects of chitosan and two microbial agents," *J. Agric. Sci.* 117:165–169 (1991).
"Aflatoxin control in postharvest corn kernels: effects of chitosan and *bacillus subtilis*," Proceedings 5th International Working Conference on Stored–Product Protection, pp. 279–290 (Fleurat–Lessard and P. Ducom, Eds.) (1992).
Hedin, P., Menn, J.J., and Hollingsworth, R.M., "Biotechnology for Crop Protection," ASC Symposium Series, 379, p. 471 (1988).
Schreiber, L.R., Gregory, G.F., Krause, C.R., and Ichida, J.M., "Production, partial purification, and antimicrobial activity of a novel antibiotic produced by *Bacillus subtilis* isolate from *Ulmus americana*," *Can. J. Bot.* 66:2338–2346 (1988).
Laemmli, U.K., "Cleavage of structural proteins during the assmebly of the head of bacteriophage T4," *Nature*, 227:680–685 (1970).
Davis, L.G., Dibner, M.D., and Battey, J.F., "Polyacrylamide Gels for Protein Separation," In *Basic Methods in Molecular Biology*, Elsevier: New York, pp. 306–310 (1986).
Trudel and Asselin, "Detection of chitinase activity after polyacrylamide gel electrophoresis," *Analytical Biochemist.*, 178 (1989).
Cuero, R.G., Smith, J.E., and Lacey, J., "A Novel Containment for Laboratory–Scale Solid Particulate Fermentations," *Biotechnology Letters* 7(7):463–466 (1985).
Payne, G., *Proceedings of the Workshop Aflatoxin in Maize* (Zuber, M.S., et al., Eds.), pp. 119–129, Mexico:CIMMYT (1987).
Cuero, R.G. et al., "Chitosan as a Control Agent of Toxigenic Fungal Growth and Aflatoxin Production," Proceedings of the Japanese Association of Mycotoxicology, Supp. No. 1, IUPAC '88 and ICPP '88, p. 194.
Cuero, R.G., et al., "N–carboxymethyl chitosan inhibition of aflatoxin production: role of Zinc," *Biotech. Letters* 13:441–444 (1991).
Cuero, R.G., et al., "Aflatoxin control in preharvest corn (Zea mays): Effects of Chitosan and Two Microbial Agents," *American Phytopathological Society/Canadian Phytopathological Society Abstract*, No. A463, Aug. 4–8 (1990).
Ghaouth, A.E., Arul, J., and Asselin, A., "Potential Use of Chitosan in Postharvest Preservation of Fruits and Vegetables," In *Advances in Chitin and Chitosan* (C. J. Brine, P. A. Sandford and J. P. Zikakis, Eds.) (1992).
Chang, D.S., et al., *Bull. Korean Fish Soc.* (22)(2): 70–78 (1989)(Abstract).
Holliday, P. (1989) A dictionary of plant pathology. University of Cambridge Press, p. 34.

*Primary Examiner*—David T. Fox
*Assistant Examiner*—Elizabeth I. McElwain
*Attorney, Agent, or Firm*—Baker & Botts, L.L.P.

[57] ABSTRACT

A method for preventing or treating microbial colonization in plants is provided. The method involves application of microorganisms such as Bacillus species or Pseudomonas species and a chitosanase inducer such as chitosan to the plants. Treatments may be made by treating the plants with a combination of the microorganism and chitosanase inducer or by sequential application of the microorganism and chitosanase inducer.

14 Claims, 2 Drawing Sheets

1. CONTROL (WATER) = 3,400

2025

2. Bsp #1 = 6,000

35  45

3. BS #2 = 6,100

55  65

4. CHITOSAN = 5,300

70  80

5. AFL = 6,200

90  100

6. Bsp #1 + CHITOSAN = 5,800

105  115

7. BS #2 + CHITOSAN = 11,000

125  135

8. CHITOSAN + AFL = 3,612

35  45

9. Bsp #1 + AFL = 4,684

55  65

10. BS #2 + AFL = 5,000

105 110

11. Bsp #1 + CHITOSAN + AFL = 14,000

115  125

12. BS #2 + CHITOSAN + AFL = 12 000

140  150

EFFECTIVE PLANT BIOCONTROL

This application is a continuation of application Ser. No. 08/147,911, filed Nov. 4, 1993 now abandoned, which is a continuation of Ser. No. 07/954,448 filed Sep. 30, 1992, now abandoned.

BACKGROUND OF THE INVENTION

Chitin is a (1-4)-linked 2-acetamido-2-deoxy-β-glucan which is naturally found in crustacean shells, microbial cell walls and insect exoskeleton. Chitosan is chemically derived by deacetylation of chitin, as described by Muzzarelli, R. A. A., "Carboxymethylated chitins and chitosans," *Carbohydrate Polymers*, 8:1–21 (1988), and incorporated herein by reference. Formation of a chitosan derivative, N-carboxymethyl chitosan (NCMC), involves blocking the amino groups of chitosan with carboxymethyl moieties. NCMC has modified biological properties and is more soluble in water than native chitosan.

Chitin and chitosan are nontoxic to rats, rabbits, hens and broilers (Arai, K., T. Kimumaki, and T. Fujita, 1968. "Toxicity of chitosan," Bulletin Tokai Register Fishery Res. Lab. 56, 89–95; and Hirano, S., et al., 1990. "Chitosan as an Ingredient for Domestic Animal Feeds," J. Agric. Food Chem. 38:1214–1217). Chitosan is rapidly absorbed by plants and increases the chlorophyll content of tomato plants (Cuero, R. G., G. Osuji, and E. Duffus. 1991. "N-Carboxymethlchitosan: Uptake and effect on chlorophyll production, water potential and biomass in tomato plants," Food Biotech. 5(2):95–103).

Chitosan and chitin are not natural components of higher plant tissues. However, their respective enzymes, chitosanase and chitinase, have been found in higher plants. They are thought to function as a defense mechanism against fungal infection (Allan, C. R. and L. A. Hadwiger, 1979. "The fungicidal effect of chitosan of fungi on varying cell wall composition," Exp. Mycol. 3:285–287; Hadwiger, L. A., B. Fristensky, and R. C. Riggleman. 1984. "Chitosan, a natural regulator of plant-fungal pathogen interactions, increases crop yields." In: *Chitin, chitosan, and related enzymes* (J. P. Zikakis, Ed.), pp. 291–302. Academic Press, Inc., New York). Inducible chitosanase has been isolated from Bacillis species in agar media, and from *B. circulans* MH-K1 (Yabuki, M. 1988. Characterization of chitosanase produced by *Bacillus circulans* MH-K1. In *Chitin and Chitosanase Sources, Chemistry Physical Properties and Applications* (G. Skjak-Braek, T. Anthonsen Conf. on Chitin and Chitosan, Trondheim, Norway, Aug. 22–24, 1988. Elsevier Applied Sciences, N.Y.) in liquid media. Fungal chitosanase from *Penicillium islandicum* has also been reported (Fenton, D. M. and D. E. Eveleigh, 1981. "Purification and mode of action of chitosanase from *Penicillium islandicum*," J. Gen. Microbiol.; 126, 151–165).

Strains of Bacillus species have been reported as growth inhibitors of pathogenic and toxigenic fungi. Cuero, et al. ("Aflatoxin control in preharvest maize: effects of chitosan and two microbial agents," J. Agric. Sci. 117:165–169 (1991); and "Aflatoxin control in postharvest corn kernels: effects of chitosan and bacillus subtilis," Proceedings 5th International Working Conference on Stored-Product Protection, pp. 279–290 (1992) (Fleurat-Lessard and P. Ducom, Eds.) demonstrated that *B. subtilis* inhibits aflatoxigenic *Aspergillus flavus* growth in preharvest corn (*Zea mays* L.) kernels, postharvest peanut (*Arachis hypogaea*), and in germinating peanut seeds.

Crops are attacked by a wide variety of fungi, including pathogenic and toxigenic molds. Occurrence of toxigenic fungi such as Aspergillus species is well documented. Corn is susceptible to fungal diseases, causing great economic losses. Corn and peanuts are two primary crops that are susceptible to preharvest infection by *A. flavus* and to concomitant aflatoxin contamination.

Corn is among the most important cereals of the world and it is used as feed and food. The moisture content of freshly harvested corn is often above the critical level for fungal development, enabling fungal proliferation after harvest. Fungi are a major cause of deterioration and spoilage in stored grain and oilseeds. Embryos of stored seeds are favored sites of infection for storage fungi. Fungal colonization can cause death of host seeds.

Cereal grains such as corn are constantly attacked by fungi, before and after harvest. In many cases this can lead to extensive or total decay by saprophytic, facultative, or parasitic fungi. Therefore, grain production will be influenced by the constant predation of fungi. Several groups of fungi can invade the kernels while they are developing on the plant or after they have matured. In corn, some of the most common invasive field fungal species are Fusarium, Cladosporium, Alternaria, and Helminthosporium. For example, *A. flavus* invades corn kernels in the field, especially after the corn has sustained insect damage.

The fungi that successfully colonize cereal grains in the field invariably require high moisture levels in the kernels. However, many of these field fungi, in particular the Fusarium species, are potent mycotoxin producers. Although drying treatments are fatal to mycotoxin-producing fungi, mycotoxins are for the most part unaffected by most drying treatments. Therefore, it is important to prevent fungal growth. During harvest and subsequent transportation and storage, other mold species such as Aspergillus and Penicillium will settle onto grain surfaces. They may be able to germinate and grow even at reduced water activity levels. Many of the well-documented toxigenic fungi, and their toxins, can cause serious contamination of stored cereals. *A. flavus* is one of the most common fungi detected in stored corn; incidence can range from 10% to 80%.

A number of methods and/or treatments, including chemical, physical, and biological methods, have been used to control and prevent fungal attack in crops such as corn and peanuts. However, developed methods have limitations and may not have practical applications. For example, microbes such as fungi develop natural resistance to pesticides. Also, an erosion in growers' profits has resulted from increasing costs of petroleum-based pesticides. Furthermore, consumer fears about use of pesticides in food products have resulted in the need for alternative treatments.

Classical and nonconventional means have been used to improve plant resistance to fungal diseases. Enhancement of natural resistance to fungal attack has been conducted by selecting quantitative traits under the control of many genes, each having a small additive effect. However, this statistical process is lengthy and complex in practice, and has a low probability of bringing together in a single crop variety all of the additive necessary for regulating plant resistance to fungal attack. Genetic engineering techniques are now being used to enhance the expression of fungal-disease resistance for crop protection (Hedin, P., J. J. Menn, and R. M. Hollingsworth, 1988. "Biotechnology for Crop Protection," ASC Symposium Series, 379, pp. 471). However, plant and fungal genomes are so poorly understood that results have been less than satisfactory to date. Biological methods have been used to prevent growth of toxigenic fungi, such as *A. flavus*, and the results have been encouraging. Although preliminary information is promising, the technology is in development and still requires field-testing. Plant extracts such as thymol, cinnamon, and clove have been found to inhibit aflatoxigenic fungi, but their mechanisms of action have not been elucidated.

Strains of Bacillus species have been reported as growth inhibitors of pathogenic and toxigenic fungi (Schreiber, L. R., C. R. Krause, and J. M. Ichida, 1988. "Production, partial purification, and antimicrobial activity of a novel antibiotic produced by *Bacillus subtilis* isolate from *Ulmus americana*," Can. J. Bot. 66:2338–2346). Cuero, et al. ("Aflatoxin control in preharvest maize: effects of chitosan and two microbial agents," J. Agric. Sci. 117:165–169 (1991); and "Aflatoxin control in postharvest corn kernels: effects of chitosan and *Bacillus subtilis*." Proceedings 5th International Working Conference on Stored-Product Protection, pp. 279–290 (1992) (Fleurat-Lessard and P. Ducom, Eds.)) demonstrated inhibition of aflatoxigenic *A. flavus* growth by strains of *B. subtilis* in preharvest corn and postharvest peanut kernels. Mutants of a strain of Bacillus species isolated from soil and treated with N-methyl-N'-nitrosoguanidine produced potent extracellular chitosanase when the cell was grown in vitro on colloidal chitosan as an inducible substance. The chitosanases have been reported as a new class of enzymes that hydrolyze chitosan. They are widely distributed in nature, and are produced by many microorganisms, including fungi, bacteria, and actinomycetes. Purified enzyme also hydrolyzes colloidal chitosan, soluble chitosan, glycol chitosan, and carboxymethylcellulose.

Chitinase has been considered to act solely as a lytic enzyme against invading fungi since its substrate, chitin, is not found in higher plants. The enzyme can also destroy fungal mycelia in vitro, and activity can be induced in plant cells by treatments with fungal components or ethylene. Chitinase activity has been elicited by chitin oligosaccharide and chitosan in melon plants and in Japanese radish, soybean, rice, hulled rice, and black pine seeds during the germination process. Although some attempts have been made to clone the chitinase gene into plants, the mechanism of action for practical application in the field is not yet understood. Recently, high-level expression of the tobacco chitinase gene in *Nicotiana sylvestris* has been demonstrated. However, progeny tests indicate that this effect is not permanent Therefore, there is an urgent need to develop an effective method for chitosanase induction in crops for practical protection against disease and fungal infection.

These and other disadvantages of the prior art are overcome by the present invention, and a new, improved process for preventing or treating disease and fungal infection in plants and seeds is provided.

SUMMARY OF THE INVENTION

It is an object of the present invention to provide a method for the treatment of plants comprising treating the plants with a therapeutically-effective dose of an effective microorganism and a chitosanase inducer so as to prevent or reduce the incidence of microbial colonization to said plants. It is an object of the present invention to provide a method for the treatment of vegetative plant tissues comprising treating the vegetative plant tissues with a therapeutically-effective dose of an effective microorganism and a chitosanase inducer so as to prevent or reduce the incidence of microbial colonization to said vegetative plant tissues. It is also an object of the present invention to provide a method for the treatment of reproductive plant tissue comprising treating the reproductive plant tissue with a therapeutically-effective dose of an effective microorganism and a chitosanase inducer so as to prevent or reduce the incidence of microbial colonization to said reproductive plant tissue. It is an object of the present invention to provide a method for the treatment of plants comprising treating the plants with a therapeutically-effective dose of an effective microorganism and a chitosanase inducer so as to prevent or reduce the incidence of fungal colonization to said plants.

It is an object of the present invention to provide a method for the treatment of plants comprising treating the plants with a therapeutically-effective dose of bacteria and a chitosanase inducer so as to prevent or reduce the incidence of microbial colonization to said plants. It is a further object of the present invention to provide said method wherein the bacteria is selected from the group consisting of Bacillus species and Pseudomonas species or mixtures thereof. It is a further object of the present invention to provide said method wherein the Bacillus is *B. subtilis*.

It is an object of the present invention to provide a method for the treatment of plants comprising treating the plants with a therapeutically-effective dose of effective microorganisms and chitosan so as to prevent or reduce the incidence of microbial colonization to said plants. Additional chitosanase inducers include chitosan salts with an acid, chitosan salts with an organic acid, chitosan salts with a carboxylic acid, glucosamine and N-carboxymethyl chitosan.

It is a further object of the present invention that the dose may be applied as a coat or a spray.

It is a further object of the present invention that the plants include Zea species, Arachis species, and Solanum species.

These and other advantages of the present invention will become apparent from the following detailed description.

DESCRIPTION OF THE INVENTION

Figure 1:
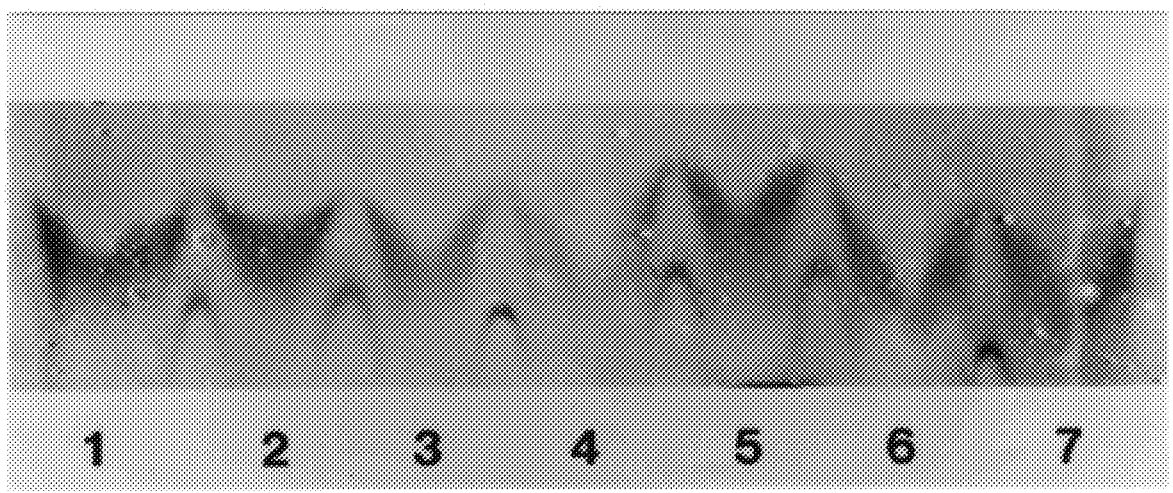
FIG. 1 depicts SDS-PAGE of the chitosanase extracted from corn (0.90 AW) treated with: (1) Water; (2) *B. subtilis* #1; (3) *B. subtilis* #2; (4) Chitosan; (5) *A. flavus*; (6) *B. subtilis* #1+Chitosan; (7) *B. subtilis* #2+Chitosan.

The present invention relates to the prevention or treatment of microbial colonization in plants and to the promotion of healthier plants by treating the plants with a therapeutically-effective amount of a chitosanase inducer and an effective microorganism. Microbial colonizations responsive to this treatment include, but are not limited to, fungal and algal colonization. Plants from the monocotyledon and dicotyledon families can be treated with the methods claimed herein. Zea species such as, but not limited to, *Z. mays* be treated. Also responsive are Arachis such as, but not limited to, *A. hypogeae*, and Solanum such as, but not limited to, *S. melongena* and *S. lycopersicon esculentum*.

Microbial colonization, such as fungal colonization, is caused by toxigenic or pathogenic fungal species. The invention preferably relates to treatment of plants invaded by aflatoxin-producing species of fungi such as, but not limited to, Aspergillus species. Preferably, the fungi are *A. flavus* or *A. parasiticus* strains. Also, pathogenic fungal colonizations such as those produced by the Botrytis species respond to the teachings of the present invention. Representative pathogenic species include, but are not limited to, *B. cinerea*. Some groups of fungi produce toxigenic and pathogenic effects. These also respond to the methods claimed in the present invention. For example, the Fusarium species such as, but not limited to, *F. graminearium* respond to the methods claimed herein. Also responsive are other Fusarium species which produce trichothecenes or zearalenones.

A person having ordinary skill in the art will be able to recognize the effectiveness of the methods disclosed and claimed herein. A therapeutically-effective amount of chitosanase inducer and an effective microorganism is that amount which significantly increases yield, enhances seed germination rate, increases chlorophyll production, delays senescence, inhibits fungal growth, and/or lowers toxin production such as, but not limited to, aflatoxin, trichothecene, or zearalenone production. The therapeutically-effective amount is that dose which may be applied directly or indirectly to the plant. The term "plant" as used herein includes, but is not limited to, vegetative and reproductive plant tissues.

It will be recognized by those skilled in the art that some microorganisms are not effective in the present invention. The effective microorganisms are those which significantly induce chitosanase activity in the plants treated. It will be appreciated that some plants are normally infected with microorganisms. Also, microorganisms may be found in some plants as normal flora. However, not all of the microorganisms which might be found in or infect plants induce chitosanase activity. Likewise, the amount of effective microorganism, if any, which may be naturally present may be insufficient to induce chitosanase activity by an amount required to treat plants as required in the present invention. A therapeutically-effective dose or amount of an effective microorganism is the amount or dose which, when combined with a chitosanase inducer, prevents or reduces the incidence of microbial colonization in plants. A therapeutically-effective amount or dose may also be recognized by visual observation of the treated plants for diseases or symptoms caused by or related to disease. Also, plants treated by the method disclosed and claimed herein will have a healthier appearance than plants not so treated.

Effective microorganisms such as, but not limited to, bacteria such as, but not limited to, Bacillus species and Pseudomonas species, and non-bacterial microorganisms such as, but not limited to, Actinomyces species, and other biological control agents which inhibit the growth of pathogenic or toxigenic fungi, induce chitosanase activity, or inhibit aflatoxin, trichothecene, or zearolene production may be employed in the present invention. Also, mixtures of any of the above may be used. Preferably, the bacteria is *B. subtilis* or *B. thermophillic.* The microbial cell population useful in the present invention may be adjusted to maximize fungal inhibition as can readily be ascertained by a person having ordinary skill in the art. The dose of microorganism required will depend on the microbial species used and the effectiveness of that species in inhibiting fungal growth in the presence or absence of a chitosanase inducing agent.

Useful microbial cell populations for crops include suspensions having about $1\times10^3$ to about $1\times10^6$ cells per ml of suspension, and preferably about $1\times10^4$ cells per ml of suspension. Effective populations are those which prevent infection while insuring germination. Useful microbial cell populations for germinating seeds are suspensions having about $1\times10^3$ to about $1\times10^4$ cells per ml of suspension, and preferably about $1\times10^3$ cells per ml of suspension.

Compounds which markedly increase induction of chitosanase activity are required in the present invention. "Chitosanase inducer" as defined herein means a compound that induces chitosanase activity. Chitosan or derivatives or fractions or subunits of chitosan which induce chitosanase activity are preferable as chitosanase inducers. A chitosan derivative which is useful in the present invention is N-carboxymethyl chitosan, but other derivatives of chitosan are expected to induce chitosanase activity and be effective in the present invention. Also useful is a chitosan salt with an acid. The acid is preferably, but not limited to, an organic acid. Organic acids most useful include mono- or dicarboxylic acids. Useful carboxylic acids include, but are not limited to, those having about one to about ten carbon atoms, and preferably about one to about five carbon atoms such as, but not limited to, formic, acetic, adipic, and lactic acids. Also useful as a chitosanase inducer is glucosamine or derivatives thereof which induce chitosanase activity.

Most preferable is a dilute solution of chitosan. The chitosanase-inducing agent such as chitosan may be prepared in an aqueous medium. Concentrations of chitosan which are effective in the present invention include aqueous solutions of about 0.001% to about 2%, preferably about 0.01% to about 1.5%, and most preferably about 0.15% (weight per volume, i.e., 1.5 grams per liter of solution). The pH of the final solution should be in the range that is not detrimental to the plant to which it is applied, which can readily be ascertained by a person having ordinary skill in the art. At low, acidic pH (pH lower than 4.0), the chitosan solution affects the physiological status of the plant. At higher pH (pH greater then 7.0), the chitosan solution has reduced solubility in an aqueous medium. The pH of chitosan solution contemplated in the present invention is about 5 to about 7, preferably about 5.2 to about 6.0, and most preferably about 5.5.

Treating is conducted by methods which bring the chitosanase inducer and microorganism into contact with the plant. For example, treatments may be made in the form of a solution or suspension of chitosanase inducer and/or microorganism. Alternatively, the chitosanase inducer and/or microorganism may be applied in mixture or in sequence as powders, solids, mists, or in any physical form which is sufficient to treat the plants.

Reproductive plant tissue (such as, but not limited to, seed) treatment applications may be conducted by treating the reproductive plant tissues with chitosanase inducer and microorganism. Treating may be conducted by any method which brings the chitosanase inducer and microorganism into contact with the reproductive plant tissue. This may be accomplished, for example, by coating the reproductive plant tissue with a solution or suspension of microorganism and chitosanase inducer. Alternatively, reproductive plant tissue treatments may be made by first treating the tissue with chitosanase inducer and subsequently treating the tissue with microorganisms. Treating is effected by any reasonable means which brings the reproductive plant tissue into contact with the microorganism and chitosanase inducer. Reproductive plant tissues may be coated by swirling the reproductive plant tissues in a container with a suspension of microorganisms and chitosanase inducer solutions. For example, reproductive plant tissues may be coated with a mixture of Bacillus (about 1×10³ cells per ml suspension) in about 0.15% final chitosan dilution (about 2 ml per about 50 grams of seed, or about 40 ml per about 1 kilogram of seed), pH 5.5.

Vegetative plant tissue (such as, but not limited to, plant leaves, stems, and roots) treatments may be made in any fashion as would be recognized by one having ordinary skill in the art that would be sufficient to treat vegetative plant tissues. Vegetative plant tissue treatment applications may be conducted by treating the tissues with chitosanase inducer and an effective microorganism. Treating may be conducted by any method which brings the chitosanase inducer and microorganism into contact with the vegetative plant tissue. This may be accomplished, for example, by treating the vegetative plant tissue with a solution or suspension of microorganism and chitosanase inducer. Alternatively, vegetative plant tissue treatments may be made by first treating the vegetative plant tissue with chitosanase inducer and subsequently treating the vegetative plant tissue with microorganisms.

Treating is effected by any reasonable means which bring the plants into contact with the microorganism and chitosanase inducer. Treating may be conducted, for example, by spraying the plants and by conducting foliar spray. Also, treating may be conducted by application of the chitosanase inducer and microorganism to the fruiting areas and/or the crown area and/or to the soil or the plant root area (rhizoplane). Those having ordinary skill in the art will recognize other methods of treating the plants which may be effective in practicing the present invention.

Field applications to monocotyledons may be made at or about the time of flowering, at or about the time the plant enters the milk stage, at or about two weeks after the milk stage, and at or about one week before harvesting. The treatments need not be applied at each of the aforementioned plant growth stages, however. Effective treatment may be achieved by fewer or more applications than those listed above. A person having ordinary skill in the art will be able to determine the most effective application times and the most cost-efficient application timetable.

Field applications to dicotyledons may be made at or about the time of flowering, at or about the fruiting time (or pegging time for peanuts and other groundnuts), at or about two weeks after fruiting or pegging, and at or about one week before harvesting. The treatments need not be applied at each of the aforementioned plant growth stages, however. Effective treatment may be achieved by fewer or more applications than those listed above. A person having ordinary skill in the art will be able to determine the most effective application times and the most cost-efficient application timetable.

A person having ordinary skill in the art will be able to ascertain the most effective amount of chitosanase inducer and microorganism to apply to vegetative plant tissue in the most economic fashion. Effective amounts of a 0.15% (wt/v) solution of chitosan and microorganism are about 100 to about 600 liters per acre, preferably about 200 to about 500 liters per acre, and most preferably about 350 to about 400 liters per acre.

Treatments may be made in two fashions. In the combined treatment regimen, the chitosanase inducer and microorganisms may be applied to the plant. In the alternative, sequential treatment regimen, the chitosanase inducer is first applied to the plant, followed by application of microorganisms. In the sequential treatment regimen, the microorganisms may be applied from a period of about 2 hours to about 3 days, preferably about 3 hours to about 48 hours, and most preferably about 3 hours to about 4 hours after application of chitosanase inducer. In the sequential application method, the chitosanase inducer should be added before application of microorganisms.

The following examples serve to illustrate specific embodiments of this invention, but should not be considered as a limitation on the scope of the invention.

1. Preparation of Chitosan

A final 0.15% chitosan solution was used for both seed coating and crop treatment, and for agar plates amendment. An original 1% solution of native chitosan (Seacure 123, Protan Lab. Inc., Seattle, Wash., U.S.A.) from crustacean shells was prepared in a water:2% acetic acid mixture (1:1 v/v) according to directions by the supplier. Further dilution of the chitosan solution was carried out to achieve the concentration to be used during the research work, i.e., 0.15%. The final pH of the chitosan solution was adjusted to 5.5. The chitosan solution was always sterilized in disposable sterile filters with 0.22 micron filters (Corning Lab. Sciences Co., N.Y.). Agar plates were prepared by amendment with chitosan (0.15% wt/v) at pH 5.5.

2. Preparation of Bacillus strains and *Aspergillus flavus* Cultures

*B. subtilis* #1, isolated from agricultural soil (Prairie View, Tex., U.S.A.), and a strain of *B. subtilis* Cohn (GUS 2000, Gustafson, Inc., Dallas, Tex., U.S.A.), herein designated as *B. subtilis* #2, were grown on nutrient agar slopes at 30° C. The cells were harvested in sterile distilled water and shaken to obtain a homogenous suspension. An isolate of *A. flavus* (NRRL 3357, Peoria, Ill., U.S.A.) was used throughout the study; this isolate was maintained on potato dextrose agar (PDA). Fresh fungal inoculum ($10^3$ spores/ml) was prepared from 3–4 day-old cultures by recovering spores in sterile water. Bacterial and fungal cell concentrations were determined by dilution plate analysis on PDA with subsequent incubation for 72 hours at 30° C. A suspension of 1×10⁵ bacterial cells per ml was used as treatment.

3. Seed Sterilization & Germinability

Each time 2 kilograms of corn seeds (*Zea mays* L. Pioneer 3369A), or peanut seeds (*Arachis hypogeae* cv Starr), were used. Corn and peanut seeds were sterilized by alternate treatments of sodium hypochlorite and hot water to achieve maximum surface sterilization and to maintain seed germinability (95%). The procedure was as follows:

a) Seeds were wrapped in a cheesecloth and immersed into 3% hypochlorite solution for 1 minute.

b) Excess hypochlorite drained-off for 3 minutes.

c) After drain-off, corn seeds were separately immersed into sterile hotwater contained in a water-bath. Corn seeds were immersed into hot water-bath at 60° C. for 30 minutes.

d) Seeds drained for 3 minutes.

e) Seeds transferred to sterile blotting paper under the laminar flow for 24 hours aseptically.

f) Germinability of seed was determined in both blotting paper and on agar plates by standard procedures.

4. Water Content Determination and Water Activity (Aw) Adjustment of Corn Seeds

Water equilibration was conducted by the Pixton and Warburton (Pixton, S. W. and S. Warburton. 1971. "Moisture content/relative humidity equilibrium of some cereal grains at different temperatures." J. Stored Prod. Res. Vol. 6, pp. 283–293) method. The initial water content of seed samples was determined by two methods: the air-oven method (Christenson, C. 1974. "Determination of water content," In

*Storage of Cereal and their products* pp. 19–48, Am. Assoc. of Cereal Chemists. St. Paul, Minn.) at 103° C. for 72 hours, and by using the electronic moisture content balance method (OHAUS-BRAINWEIGH MB 301, Forham Park, N.J., U.S.A.). Samples were then conditioned to 0.90 Aw by adding the required sterile water according to the following equation:

$$X = \frac{W(Y-a)}{100-Y}$$

where X represents the water to be added (ml); Y represents the required moisture content; W represents the weight or amount of seed to be used; and "a" represents the initial moisture content.

The required volume of water was added to each flask which was then hermetically sealed with a tight-fitting rubber bung stopper to avoid loss of moisture, and stored at 5° C. to prevent microbial contamination. The flasks were shaken vigorously each day for 5–7 days until water equilibration of seeds was achieved.

5. Seed Extraction for Chitosanase Assays

After 4 days of incubation, seed samples were ground under liquid nitrogen conditions (10 g seeds per 10 ml of 0.1M Tris-HCl, pH 8.0) using a caryogenic IKA-A 10 analytical mill (Tekmar Co., Cincinnati, Ohio, U.S.A.). Ground samples were then centrifuged at 12,000×g for 20 min; the supernatants (chitosanase extracts) were used for enzyme assays by the following techniques:

A) Polyacrylamide Gel Electrophoresis (PAGE): Chitosanase assays were carried out by SDS-Polyacrylamide Gel Electrophoresis (SDS-PAGE). SDS-PAGE was conducted in 7.5% gel according to the method of Laemmli (Laemmli, U.K. 1970. "Cleavage of structural proteins during the assembly of the head of bacteriophage T4." Nature 227:680–685) in Tris-glycine-buffer, pH 8.9. The enzyme substrate (0.02% glycol-chitosan) was copolymerized with acrylamide. Enzyme extract was mixed with an equal volume of sample buffer with SDS (Davis, L. G., M. D. Dibner, J. F. Battey, 1986. "Polyacrylamide Gels for Protein Separation." In *Basic Methods in Molecular Biology*. Elsevier: New York, pp. 306–310), then 50 µl of sample (equivalent to extract from 25 mg of seed) were loaded into the gel wells; the electrophoresis was set for 14 h at 40 volts. At the end of the electrophoresis, the SDS in the gel was removed with 0.1M sodium acetate buffer, pH 5, containing 1% Triton X-100 by modification of the method by Trudel and Asselin ("Detection of chitinase activity after polyacrylamide gel electrophoresis." Analytical Biochemist. 178, 1989). Enzyme activity was observed after washing the gel with Triton solution for 30 minutes at 30° C. Enzyme activity was determined by densitometric scanning of the gel using a Shimatzu Dual-Wavelength Flying Spot Scanning densitometer (CS-9000U model, Columbia, Md., U.S.A.) at 450 nm. The densitometric area was related to chitosanase activity per mg of seed fresh weight for quantitation of chitosanase induction. After 30 minutes of development with Triton X-100 solution, seed-chitosanase activity in the PAGE showed as a clearing V-shape digestion of the substrate (glycol-chitosan).

B) Radialmetric Quantitation of Chitosanase: Enzyme radialmetric analysis was conducted on agar plates containing chitosan (0.15% wt/v) as substrate. Seed chitosanase extracts (200 ul) were blotted onto the discs (25 mm diameters), aseptically transferred to the center of the chitosan-agar plates, and then incubated for 4 days at 30° C. The enzyme activity was determined by the area of the clearing (halo) formed around the disc. For quantitation of chitosanase induction, the area was determined by densitometric scanning of the chitosan-agar plates at 450 nm under reflection light beam, and measured by a Quanta-Scan 2-Dimensional Analysis Software Program (P/N 206-18597) (Shimatzu Co., Columbia, Md., U.S.A.) attached to an IBM clone with chromatography software. The quantitated densitometric area was related to chitosanase activity per mg of corn fresh weight.

7. Seed Treatment Application with Bacillus and Chitosan

Subsequent treatments included soaking the seeds in Bacillus cells suspension with or without chitosan, and/or in aqueous *A. flavus* spore suspension (2 ml/50 g of seed). A suspension of $10^5$ cells/ml of each Bacillus strain, or $10^3$ spore/ml of *A. flavus* in 0.15% final chitosan dilution was prepared. The seeds were coated with this mixture (2 ml per 50 g of seed or 40 ml per Kg of seed) for 1 minute at room temperature. The coating was conducted by swirling in a 250 ml sterile beaker. After coating, seeds were aseptically air dried under laminar flow for 30 minutes. Treatments included 10 controls:

1) water alone
2) *B. subtilis* #1 alone
3) *B. subtilis* #2 alone
4) Chitosan
5) *A. flavus* alone
6) *B. subtilis* #1+Chitosan
7) *B. subtilis* #2+Chitosan
8) Chitosan+*A. flavus*
9) *B. subtilis* #1+*A. flavus*
10) *B. subtilis* #2+*A. flavus*

The experimental triple treatments were:

11) *B. subtilis* #1+Chitosan+*A. flavus*
12) *B. subtilis* #2+Chitosan+*A. flavus*.

After seeds were treated, samples were transferred to a microporous bag containment system (Cuero, R. G., J. E. Smith, and J. Lacey, 1985. "A Novel Containment for Laboratory-Scale Solid Particulate Fermentations," *Biotechnology Letters* 7(7):463–466) aseptically. This system provides a sterilized aerobic environment in which the treated and/or inoculated substrate (peanut or corn seeds) could be maintained during the experiment at constant temperatures and Aw, allowing diffusion of gases, but preventing cross-contamination of microorganisms. Such a system facilitates the study of microbial growth, enzyme, and toxin production in a natural solid substrate under conditions close to those found in a natural environment. The microporous film-bags are made of perforated polyethylene material having very small pores (0.4 microns). The pores exclude microorganisms, but allow efficient air and water transmission. The size of the bags used were 13×23 cm., and they were heat sterilized before use. The bags were aseptically filled with separate corn or peanut seed samples (50 g/bag) and immediately sealed. Three bags per treatment were used. The bags were gently shaken every day. The bags containing the seed samples were then incubated at 25° C. and 90% relative humidity (RH) for 4 days in a Percival Environmental Cabinet (Boone, Iowa, U.S.A.). After 4 days' incubation, microbial growth (CFU) and chitosanase were determined using the techniques described herein.

Growth of Bacillus #1 & #2 and *A. flavus* in corn and peanut seeds was quantitated by colony-forming unit (CFU) using the standard dilution plate count method on PDA. Microbial quantitation was conducted after 4 days of incubation at 30° C.

Figure 2:
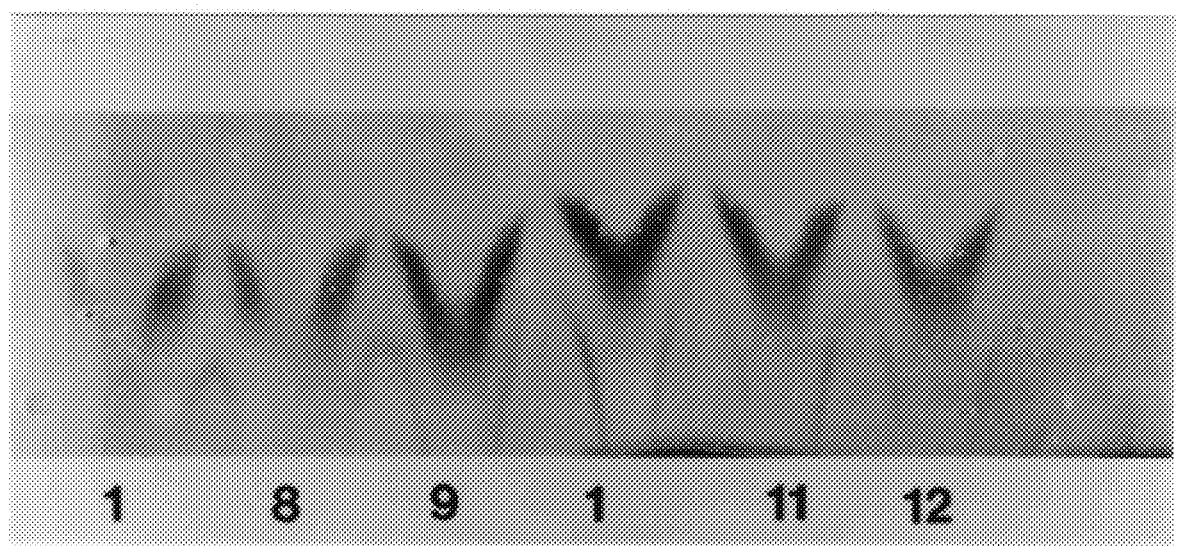
FIG. 2 depicts SDS-PAGE of the chitosanase extracted from corn (0.90 AW) treated with: (8) Chitosan+*A. flavus*; (9) *B. subtilis* #1+*A. flavus*; (10) *B. subtilis* #2+*A. flavus*; (11) *B. subtilis* #1+Chitosan+*A. flavus*; (12) *B. subtilis* #2+Chitosan+*A. flavus*.
Figure 3:
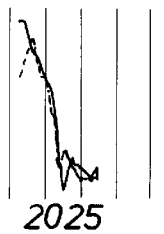
FIG. 3 depicts chitosanase induction in corn (0.90 AW) after single or combined treatments with: (1) Water; (2) *B. subtilis* #1; (3) *B. subtilis* #2; (4) Chitosan; (5) *A. flavus*; (6) *B. subtilis* #1+Chitosan; (7) *B. subtilis* #2+Chitosan; (8) Chitosan+*A. flavus*; (9) *B. subtilis* #1+*A. flavus*; (10) *B. subtilis* #2+*A. flavus*; (11) *B. subtilis* #1+Chitosan+*A. flavus*; (12) *B. subtilis* #2+Chitosan+*A. flavus*.
Figure 3:
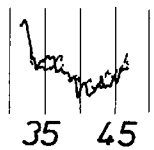
Figure 3:
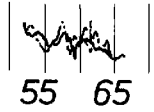
Figure 3:
Figure 3:
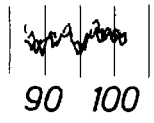
Figure 3:
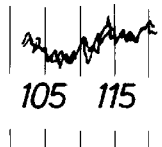
Figure 3:
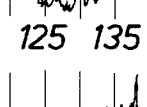
Figure 3:
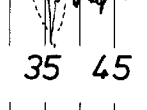
Figure 3:
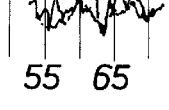
Figure 3:
Figure 3:
Figure 3:

FIGS. 1 and 2 demonstrate presence of chitosanase enzyme after PAGE of extracts of treated germinating corn. Chitosanase activities were quantified by densitometry (FIG. 3); the results are shown in Table 1.

TABLE 1

Chitosanase Activity in Germinating Corn Expressed as Densitometric Area mg$^{-1}$ of Corn Fresh Weight.

| TREATMENT | DENSITOMETRIC AREAS[1] | |
|---|---|---|
| | ELECTRO-PHORETIC GEL AREA | CHITOSAN-AGAR DISC AREA |
| 1. Water | 136 | Nil Area |
| 2. B. subtilis #1 | 240 | 16 |
| 3. B. subtilis #2 | 244 | 16 |
| 4. Chitosan | 212 | 18 |
| 5. A. flavus | 248 | 17 |
| 6. B. subtilis #1 + Chitosan | 232 | 17 |
| 7. B. subtilis #2 + Chitosan | 400 | 18 |
| 8. Chitosan + A. flavus | 344 | 17 |
| 9. B. subtilis #1 + A. flavus | 187 | 17 |
| 10. B. subtilis #2 + A. flavus | 200 | 15 |
| 11. B. subtilis #1 + Chitosan + A. flavus | 560 | 16 |
| 12. B. subtilis #2 + Chitosan + A. flavus | 504 | 13 |

[1]Densitometric Area per mg fresh weight of corn.

All treatments induced more chitosanase than the non-treated (water). Combined treatments (#11 & #12) containing the three treatments (*B. subtilis*, chitosan, and *A. flavus*) showed the highest chitosanase induction (above 500 densitometric area/mg corn); the other treatments (from #2 to #10) containing single and/or double treatments induced lower chitosanase activity, which never exceeded 400 densitometric area/mg corn. On the contrary, the control which did not receive microbial and chitosan treatments showed the lowest chitosanase activity (less than 100 densitometric area/mg corn).

The activity of the chitosanase (radialmetric assay) is seen as a clearing (halo) area around the paper disc on agar plates. The activities of the enzyme (halo area) which were quantitated by two-dimensional scanning densitometry are shown in Table 1. The results show that all treatments containing bacteria and/or chitosan induced chitosanase, while the control without bacteria and chitosan treatments showed no detectable enzyme activity (halo area). Therefore, the radialmetric analysis confirms the PAGE results.

Growth of *A. flavus* was markedly reduced (100-fold) by the combined treatments (#11 & #12) containing chitosan+ either strain of *B. subtilis* species +*A. flavus* in germinating corn seeds, after 4 days' incubation while other treatments (#8, #9, & #10) containing either chitosan or one of the Bacillus strains in combination with *A. flavus* inhibited fungal growth ten-fold only, as compared to control treatment (#5) containing *A. flavus* alone (Table 2).

TABLE 2

Microbial Counts (CFU) of Treated Germinating Corn Incubated at 30° C./90% RH after 4 days[1].

| TREATMENT | MEANS OF CFU[2] | |
|---|---|---|
| | AFL | B. subtilis |
| 1. Water | 0 | 0 |
| 2. B. subtilis #1 | 0 | 6.5 × 10³ |
| 3. B. subtilis #2 | 0 | 1.7 × 10⁵ |
| 4. Chit | 0 | 0 |
| 5. A. flavus | 2.3 × 10⁴ | 0 |
| 6. B. subtilis #1 + Chit | 0 | 2.3 × 10⁴ |
| 7. B. subtilis #2 + Chit | 0 | 3.3 × 10³ |
| 8. Chit + A. flavus | 4 × 10³ | 0 |
| 9. B. subtilis #1 + AFL | 2.3 × 10³ | 5.3 × 10³ |
| 10. B. subtilis #2 + AFL | 1 × 10⁴ | 5 × 10⁴ |
| 11. B. subtilis + Chit + AFL | 5 × 10² | 3 × 10³ |
| 12. B. subtilis #2 + Chit + AFL | 2.3 × 10² | 4 × 10³ |

[1]Aw of Corn = 0.90
[2]CFU = Colony Forming Unit
AFL = *Aspergillus flavus*
Chit = Chitosan The data show the direct relationship between the effective control of *A. flavus* growth and the enhanced level of chitosanase induction (see Table 1) by treatments (#11 & #12) chitosan+either strain of *B. subtilis*.

Similar observations were made for germinating peanut as shown in Table 3.

TABLE 3

Microbial Counts (CFU) of Treated Germinating Peanut Incubated at 30° C./90% RH after 4 days[1].

| TREATMENT | MEANS OF CFU[2] | |
|---|---|---|
| | AFL | B. subtilis |
| 1. Water | 0 | 0 |
| 2. B. subtilis #1 | 0 | 1.5 × 10⁶ |
| 3. B. subtilis #2 | 0 | 8 × 10⁸ |
| 4. Chit | 0 | 0 |
| 5. A. flavus | 3 × 10⁵ | 0 |
| 6. B. subtilis #1 + Chit | 0 | 3.6 × 10⁴ |
| 7. B. subtilis #2 + Chit | 0 | 2.6 × 10⁵ |
| 8. Chit + A. flavus | 3 × 10⁴ | 0 |
| 9. B. subtilis #1 + AFL | 1 × 10⁴ | 4.3 × 10⁴ |
| 10. B. subtilis #2 + AFL | 1.8 × 10⁴ | 1.3 × 10⁴ |
| 11. B. subtilis #1 + Chit + AFL | 1.8 × 10³ | 1 × 10⁴ |
| 12. B. subtilis #2 + Chit + AFL | 1 × 10³ | 5.5 × 10⁴ |

[1]Aw of Peanut = 0.90
[2]CFU = Colony Forming Unit
AFL = *Aspergillus flavus*
Chit = Chitosan Combined treatment with bacteria+chitosan again controlled *A. flavus* (100-fold). Treatments of chitosan and either strain of *B. subtilis* controlled *A. flavus* growth about 10-fold.

8. Field Crop (Preharvest Corn) Treatment with Bacillus and Chitosan

Field plot trials were conducted on the Prairie View A&M University Farm area near Waller County, Texas to test the efficacy of the herein-presented method. A randomized complete block design (16 treatment X 4 replicate/treatment) was used, with each block consisting of 16 treated rows and 2 guard rows. Corn seed (cultivar B73xMO/7) susceptible to *A. flavus* infection was planted. Two experiments were carried out: 1) single treatments, including use of independent control agents, and 2) mixed treatments, including a combination of agents.

Inoculation and Treatment Application: Various treatments were applied 2 days before or 2 days after *A. flavus* inoculation. Single treatments included: a) chitosan and b) *B. subtilis* #2. Combined treatments included: a) chitosan+*B. subtilis* #2. Control treatments consisted of plants inoculated with *A. flavus* alone, chitosan alone, or sterile water alone.

From plots containing about 160 test plants, ten plants were randomly selected for each treatment replicate. Ears were inoculated with a suspension of *A. flavus* spores applied alone or in mixture with chitosan or microbial suspensions at 20 days after flowering. Dosage rate per acre was 20 gallons. Inoculations of *A. flavus* and *B. subtilis* #2 were conducted using the pinbar technique (Payne, G., *Proceedings of the Workshop Aflatoxin in Maize* (Zuber, M. S., et al., Eds.), pp. 119–129 (1987) Mexico: CIMMYT; and Scott & Zummo, *Proceedings of the Workshop Aflatoxin in Maize.* (Zuber, M. S., et al., Eds.), pp. 221–232 (1987) Mexico: CIMMYT) to mimic insect damage. Sterile pinbars (6 cm×3 cm) with three rows of equally distributed needles (36 in total) were used to make multiple-puncture injury through the husk to the developing kernels. Pinbar injury was introduced three times around each ear (36×3=108 puncture injuries/ear). A sterile pinbar was used for each treatment. Immediately after ear puncturing, *A. flavus* inocula and/or control treatments were applied either singly or in combination. Treatments were applied (5 ml to each ear) by aerosol sprays from a pressurized (15 p.s.i.) bottle. At maturity, ten ears were collected from each plot at random and dried to a final kernel moisture content of 14% or below. Dried ears were hand shelled and a 100-grain sample was taken for plating.

*Fungal Determination from Field Corn: A. flavus* determination was conducted by plating five surface-sterilized kernels (2% sodium hypochlorite for 2 min), on PDA in each of ten plates/sample; plates were incubated for 5 days at 25° C. and kernels evaluated for *A. flavus* presence using the technique described by Cuero, R. G., J. E. Smith, and J. Lacey, 1985. "A Novel Containment for Laboratory-Scale Solid Particulate Fermentations," Biotechnology Letters 7(7):463–466.

Growth of *A. flavus* was markedly controlled (97%) by combined treatment of chitosan+*B. subtilis* (#2) when applied either 48 hours before or after inoculation with *A. flavus* in preharvest corn kernels (Table 4).

TABLE 4

Mean *Aspergillus flavus* counts in corn kernels at harvest after single and combined treatments. (Underlined component of a treatment aggregate was applied 48 h earlier than other treatment fractions.)

| Treatment | *A. flavus* mean occurrence (%) | S.E. (6 D.F.) |
|---|---|---|
| *A. flavus* alone | 30.0 | 3.6 |
| *A. flavus* + chitosan | 1.7 | 1.7 |
| Chitosan + *A. flavus* | 3.3 | 2.1 |
| *A. flavus* + *B. subtilis* | 6.7 | 2.1 |
| *B. subtilis* + *A. flavus* | 6.7 | 2.1 |
| *A. flavus* + chitosan + *B. subtilis* | 8.3 | 1.7 |
| Chitosan + *B. subtilis* + *A. flavus* | 8.0 | 2.0 |

It was also observed that these combined treatments retarded corn plant senescence. After 5 months of growth, treated corn plants were still largely green, whereas the non-treated (control) were becoming senescent. This is perhaps due to reduction of fungal attack and/or the effect of chitosan in enhancing the chlorophyll content.

Many other variations and modifications may be made in the techniques hereinbefore described, by those having experience in this technology, without departing from the concept of the present invention. Accordingly, it should be clearly understood that the invention described in the foregoing description is illustrative only and is not intended as a limitation on the scope of the invention.

What is claimed is:

1. A method for inhibiting Aspergillus growth on plant tissues consisting essentially of the steps of:

a) treating the plant tissues with bacteria selected from the group consisting of species of Pseudomonas and Actinomyces; and b) treating the plant tissues with a chitosanase inducer to inhibit Aspergillus growth.

2. A method according to claim 1 wherein the plant tissues treated comprise vegetative plant tissues.

3. A method according to claim 1 wherein the plant tissues treated comprise reproductive plant tissues.

4. A method according to claim 1 wherein the chitosanase inducer is selected from the group consisting of chitosan and salts and derivatives of chitosan.

5. A method according to claim 1 further comprising the step of mixing the chitosanase inducer with an acid.

6. A method according to claim 5 wherein the acid is an organic acid.

7. A method according to claim 6 wherein the organic acid is a carboxylic acid.

8. A method according to claim 1 wherein the chitosanase inducer is selected from the group consisting of a glucosamine and salts and derivatives of glucosamine.

9. A method according to claim 1 wherein the chitosanase inducer is N-carboxymethyl chitosan.

10. A method according to claim 1 wherein the plant tissues are treated with a spray of bacteria.

11. A method according to claim 10 wherein the spray is a foliar spray.

12. A method according to claim 1 wherein the plant tissues comprise rhizoplane.

13. A method according to claim 1 wherein the plant tissues are selected from the group consisting of species of Zea, Arachis, and Solanum.

14. A method according to claim 1 wherein the plant tissues are first treated with the chitosanase inducer, followed by treatment with the bacteria.

* * * * *